(12) United States Patent
Pinna et al.

(10) Patent No.: US 7,399,494 B2
(45) Date of Patent: *Jul. 15, 2008

(54) QUICK WATER-DISSOLVED FILM PRODUCT, FOR TREATING MILK WITH BACTERIA AND/OR ENZYMES

(75) Inventors: Marco Pinna, Iduno Olona (IT); Fausto Pinna, Lesmo (IT)

(73) Assignee: Biofarmitalia S.p.A., Milan (IT)

( * ) Notice: Subject to any disclaimer, the term of this patent is extended or adjusted under 35 U.S.C. 154(b) by 744 days.

This patent is subject to a terminal disclaimer.

(21) Appl. No.: 10/680,115

(22) Filed: Oct. 8, 2003

(65) Prior Publication Data

US 2004/0086599 A1    May 6, 2004

(30) Foreign Application Priority Data

Nov. 5, 2002    (IT)    ............................ MI2002A2344

(51) Int. Cl.
*A23C 9/137*    (2006.01)
(52) U.S. Cl. ............................ 426/42; 426/61; 426/96; 426/573; 426/578
(58) Field of Classification Search ................... 426/96, 426/42, 61, 573, 578; 424/443, 441, 484, 424/488, 93.45, 94.1; 435/174, 177, 179, 435/182
See application file for complete search history.

(56) References Cited

U.S. PATENT DOCUMENTS

| | | | |
|---|---|---|---|
| 3,677,897 A | | 7/1972 | Jeffreys |
| 3,897,307 A | | 7/1975 | Porubcan et al. |
| 4,115,292 A | | 9/1978 | Richardson et al. |
| 4,345,032 A | * | 8/1982 | Hata .................. 435/252.9 |
| 4,418,147 A | | 11/1983 | Muetgeert et al. |
| 5,206,026 A | * | 4/1993 | Sharik .................. 424/445 |
| 6,419,903 B1 | * | 7/2002 | Xu et al. .................. 424/49 |
| 6,497,887 B1 | * | 12/2002 | Zecchino et al. ............ 424/401 |
| 2003/0096002 A1 | * | 5/2003 | Borek et al. ................. 424/452 |

FOREIGN PATENT DOCUMENTS

| | | |
|---|---|---|
| GB | 1 286 095 | 8/1972 |
| WO | 02/094224 A1 * | 11/2002 |

* cited by examiner

*Primary Examiner*—Arthur L Corbin
(74) *Attorney, Agent, or Firm*—Oblon, Spivak, McClelland, Maier & Neustadt, P.C.

(57) ABSTRACT

High solubility film product comprising a starch and/or a cellulose and at least one bacterium or enzyme chosen from those necessary for milk fermentation, coagulation or curdling.

17 Claims, No Drawings

QUICK WATER-DISSOLVED FILM PRODUCT, FOR TREATING MILK WITH BACTERIA AND/OR ENZYMES

FIELD OF THE INVENTION

The subject of the present invention is a quick water-dissolved film product, for treating milk with bacteria and/or enzymes

BACKGROUND OF THE INVENTION

To obtain milk by-products or derivatives such as yoghurt, cheese, butter, cream, etc., it is known to subject the milk to treatment with lactic acid cultures, coagulant substances and/or other microorganisms.

These processes, which utilize well known ancient procedures and techniques, use lactic acid cultures, coagulant substances such as bovine rennet or other microorganisms, generally in liquid or lyophilized form.

Both the liquid form and the lyophilized form present considerable drawbacks, both with regard to the stability of the microorganisms and their life duration, and with regard to the dosage.

In this respect, it is known that the liquid form possesses a high risk of bacterial contamination and moulds extraneous to those considered useful, the flora present therein rapidly evolving to modify the content (number) of useful microbacteria.

With regard to the lyophilized form, being strongly hygroscopic and hence influenced by moisture and temperature changes, it requires sophisticated procedures for correct preservation, otherwise there is the risk of contamination and alteration. Such preparations are suitable mainly for large or medium transformation firms, which can avoid prolonged storage of raw materials and can process considerable quantities of milk for each preparation, hence totally utilizing dosages ready prepared in bags for 500 or 1000 kg of milk, without having the problem of storing and preserving the remainder.

In contrast, small and medium enterprises process small or medium milk quantities at a time and do not possess adequate structures for correct storage of raw materials which can deteriorate. It would therefore be advantageous to have available a product with a sufficiently precise microorganism content for use in a single dose for small milk quantities, or in several doses for larger milk quantities, which is easily preservable, and is ready for use being immediately dissolvable in water or milk. The use of known technologies to obtain solid supports dissolvable in water represents a limit, as the production of tablets or other similar forms requires processing techniques, such as high pressure, which would destroy the highly heat-sensitive and pressure-sensitive flora. Another limit is that the production of these supports often requires considerable quantities of ethanol or other alcohols which for food bacteria, such as probiotic, prebiotic and symbiotic lactic acid cultures, would be destructive. This applies in particular to all groups of lactic acid bacteria (*lactobacillus acidophilus, lactobacillus gasseri, lactobacillus johsonii, lactobacillus crispatus, lactobacillus amylovorus, lactobacillus gallinarum; lactobacillus casei* subsp. casei, *lactobacillus paracasei* subsp. paracasei, *lactobacillus rhamnosus; lactobacillus reuteri, lactobacillus plantarum, lactobacillus salivarius, pediococcus acidilactici, lactobacillus delbrueckii* subsp. bulgaricus, *Steptococcus thermophilus*, etc.), all the bifidobactera (*bifidobacterium longum, bifidum, breve, infantis, adolescentis, lactis*, etc.), and other microorganisms (non-lactic acid bacteria and non-bifidobacteria) (*Enterococcus faecium, bacillus subtilis, bacillus coagulans* (*Lactobacillus sporogenes*), *saccharomyces cerevisiae*, etc.). Hence if they could be kept alive in a metered quantity in large number on a support dissolvable in milk or water, interest would be considerable in all dairy milk processes for which. products could hence be provided in quickly dissolvable solid film form of known strength ready for easy and immediate use.

SUMMARY OF THE INVENTION

The present invention provides a product in edible film form which obviates the aforesaid drawbacks while containing the desired quantities of lactic acid cultures, coagulant substances such as bovine rennet or other microorganisms.

The film product of the invention consists of a solid support comprising at least one substance chosen from the group formed from at least one starch of low molecular weight and high amylopectin content and from at least one cellulose compatible with said starch, and is characterised in that said solid support incorporates at least one bacterium or enzyme of the type commonly used for milk treatment.

Preferably, said bacteria and enzymes consist of probiotic, prebiotic and/or symbiotic lactic acid cultures.

The product in solid film form has good dimensional stability, such as to be obtainable with a very small thickness (between 10 and 70 microns) so that it can be die-cut or sheared into small or medium formats easily insertable into containers suitable for milk processing, and which are quickly dissolved when in contact therewith.

To obtain the aforedescribed product, numerous tests have shown that the use of least one of the following elements is preferred:

a) at least one low molecular weight starch of high amylopectin content. The starch can be selected from those obtained from maize, wheat, potato, rice, soya, tapioca, etc., this starch being present between a minimum of 20% and a maximum of 80% by weight on the weight of the film product.

b) at least one cellulose and/or polymer compatible with said starch, preferably chosen from the following substances: hydroxypropylcellulose, hydroxypropylmethylcellulose, hydroxyethylcellulose, carboxymethylcellulose, polyvinyl alcohol, polyvinylpyrrolidone, polyethylene glycol, xanthan gum These polymers and celluloses are preferably present in the finished product (film) from a minimum of 15% to a maximum of 70% by weight.

Other ingredients the presence of which is preferred in producing the film are polysorbate 80, sorbitol, glycerol mono oleate, carrageenan, soya lecithin, colorants and methylsalicylate.

The procedure preferably followed to bind the starch and cellulose in stable form is to dilute the starch and cellulose in ethanol and water in a jacketed mixer then, while agitating, bringing them to a temperature of 80÷90° C. and maintaining them under agitation for at least 30 minutes to substantially eliminate the ethanol. Again while agitating, the mixture is brought to a temperature around 30÷35° C. until a viscosity of 3÷8000 mPas is obtained. The product obtained in this manner is able to retain considerable quantities of microorganisms and useful substances, up to 30% by weight of its own weight: after evaporating all the residual water, active substance percentages between 10% and 50% by weight on the finished product are achieved. Moreover, once the mixture has cooled to 30÷35° C. and having lost its ethanol load, alcohol-sensitive substances such as lactic acid cultures, microorganisms and bacteria can be added to the mixture. This mixture is maintained under agitation and passed through a doctor blade assembly which does not compress the product and is able to distribute the product in the form of a thin film onto an antiadherent support which travels through a ventilated tunnel heated to 30÷35° C. to evaporate the residual water and to form the final film. This film is then separated from the anti-adherent support by known methods and die-cut into the required shape and size, then inserted into the final package.

DETAILED DESCRIPTION OF THE INVENTION

The features of the present invention will be more apparent from the ensuing non-limitative Examples.

EXAMPLE 1

The components of two separate phases known as "Phase A" and "Phase B" are used.

Phase A comprises:

| | |
|---|---|
| H$_2$O | 150 g |
| ethanol | 150 g |
| hydroxypropylmethylcellulose | 50 g |
| oxidized starch | 20 g |
| polyvinyl alcohol | 15 g |
| polyethylene glycol | 4 g |
| glycerin | 2 g |
| sorbitol | 2 g |
| colorant | |

Phase B comprises a mixture of lyophilized streptococcus thermophilus (15 g) and lyophilized lactobacillus rhamnosus (15 g).

The components of Phase A are fed into a jacketed closed mixer in the following succession: water, ethanol and oxidized starch are firstly fed and agitated at medium speed and the temperature brought to 80° C., agitation being continued until the starch has dissolved and caramelized, to obtain a homogeneous solution.

While agitating, the temperature is brought to 90° C. and agitation maintained (at about 60 r.p.m.) for 30 minutes, then hydroxypropylmethylcellulose, polyethylene glycol and colorant are added and agitation continued until the solution is homogeneous.

It is cooled to 35° C., glycerol and sorbitol are added and agitation is maintained for 15 minutes. The temperature is brought to 30° C. and Phase B is slowly added. Agitation is maintained for 15 minutes. Using a peristaltic pump, the mixed product is withdrawn and made to flow onto a doctor blade assembly heated to 30° C., through which there passes a siliconized polyester web on which the product is deposited as a film to a thickness of 70 microns. The product (film on polyester) is passed through a forced-air oven heated to 35° C. On leaving the oven the film is detached from the polyester support, it is die-cut with a roller die into 4.6×6.6 cm rectangles, and the rectangles obtained are inser container which is sealed.

Each rectangle obtained has a thickness of 35 microns, the time for its dissolving in water being 6 seconds. The quantities of microorganisms present are measured by a microscope, the result being the following:

| | |
|---|---|
| weight of rectangle (4.6 × 6.6 cm) | 100 mg |
| quantity of bacteria present | 1.8 × 10$^3$ u |

EXAMPLE 2

As in Example 1 the components of two different compositions known as "Phase A" and "Phase B" are used.

The components of Phase A are:

| | |
|---|---|
| H$_2$O | 150 g |
| ethanol | 150 g |
| hydroxyethylcellulose | 50 g |
| polyvinyl pyrrolidone | 25 g |
| hydroxypropylmethylcellulose | 35 g |
| oxidized starch | 20 g |
| xanthan gum | 10 g |
| polysorbate 80 | 2 g |
| methyl salicylate | 2 g |
| sorbitol | 2 g |
| colorant | |

The components of Phase B consist only of lyophilized bifidobacterium breve (40 g).

The components of Phase A, i.e. water, ethanol and oxidized starch, are firstly fed into a jacketed closed mixer, then agitated at medium speed and the temperature brought to 80° C., agitation then being continued until a homogeneous solution is obtained.

While agitating, the temperature is brought to 90° C. and agitation maintained for 30 minutes, then hydroxyethylcellulose, polyvinyl pyrrolidone, hydroxypropylmethylcellulose, xanthan gum and colorant are added and agitation continued until the solution is homogeneous.

It is cooled to 35° C., polysorbate 80, methylsalicylate and sorbitol are added and agitation is maintained for 15 minutes.

The temperature is brought to 30° C. and Phase B is slowly added. Agitation is maintained for 15 minutes. Using a peristaltic pump, the mixed product is withdrawn and made to flow onto a doctor blade assembly heated to 30° C., through which there passes a siliconized polyester support web on which the product is deposited as a film to a thickness of 70 microns. The product deposited as a film on the polyester web is passed through a forced-air oven heated to 35° C. On leaving the oven the film is detached from the polyester support, it is die-cut with a roller die into 4.6×6.6 cm rectangles. The rectangles so obtained are packaged in a sealed container.

The rectangles obtained have a thickness of 40 microns, the time for their dissolving in water being 6 seconds. The quantities of bacteria present are measured by a microscope, the result being the following:

| | |
|---|---|
| weight of each rectangle (4.6 × 6.6 cm) | 121 mg |
| quantity of bifidobacterium breve present | 2 × 10$^3$ u |

EXAMPLE 3

As in the preceding examples, components of Phase A and components of Phase B are used.

The components of Phase A are:

| | |
|---|---|
| H₂O | 150 g |
| ethanol | 150 g |
| hydroxypropylmethylcellulose | 50 g |
| oxidized starch | 40 g |
| carrageenan | 10 g |
| polyethylene glycol 400 med | 4 g |
| soya lecithin | 10 g |
| methyl salicylate | 1 g |
| colorant | |

Phase B is formed from lyophilized *Lactobacillus casei* (40 g).

Phase A is fed into a jacketed closed mixer in the following manner: water, ethanol and oxidized starch, are firstly fed in, then agitated at medium speed and the temperature brought to 80° C., agitation then being continued until dissolution takes place to obtain a homogeneous solution. While agitating, the temperature is brought to 90° C. and agitation maintained for 30 minutes, then hydroxypropylmethylcellulose, carrageenan and colorant are added and agitation continued until the solution is homogeneous.

It is cooled to 35° C., polyethylene glycol 400 med, soya lecithin and methylsalicylate are added and agitation is maintained for 15 minutes. The temperature is brought to 30° C. and Phase B is slowly added, and agitation is maintained for 15 minutes.

Using a peristaltic pump, the mixed product is withdrawn and made to flow onto a doctor blade assembly heated to 30° C., through which there passes a siliconized polyester support web on which the product is deposited as a film to a thickness of 70 microns. The product deposited as a film on the polyester web is passed through a forced-air oven heated to 35° C. On leaving the oven the film is detached from the polyester support, it is die-cut with a roller die into 4.6×6.6 cm rectangles. The rectangles obtained are packaged in a hermetically sealed container.

Each rectangle obtained has a thickness of 33 microns, the time for its dissolving in water being 5 seconds. The quantities of bacteria present are measured by a microscope, the result being the following:

| | |
|---|---|
| weight of rectangle (4.6 × 6.6 cm) | 1041 mg |
| quantity of Lactobacillus casei | 1.4 × 10³ u |

EXAMPLE 4

Again a Phase A comprising:

| | |
|---|---|
| H₂O | 150 g |
| ethanol | 150 g |
| oxidized starch | 60 g |
| hydroxypropylmethylcellulose | 50 g |
| carrageenan | 10 g |
| polyethylene glycol | 4 g |

-continued

| | |
|---|---|
| glycerol | 2 g |
| sorbitol | 2 g |
| colorant | | together with a Phase B comprising food bacteria consisting of 100 g of lyophilized *lactobacillus paracasei* are used.

Phase A is fed into a jacketed closed mixer in the following manner: water, ethanol and oxidized starch, are firstly fed in, then agitated at medium speed and the temperature brought to 80° C., agitation then being continued until the starch has dissolved to obtain a homogeneous solution.

While agitating, the temperature is brought to 90° C. and agitation maintained for 30 minutes, then hydroxypropylmethylcellulose, carrageenan and colorant are added and agitation continued until the solution is homogeneous. It is cooled to 35° C., polyethylene glycol 400 med, glycerol and sorbitol are added and agitation is maintained for 15 minutes. The temperature is brought to 30° C. and the probiotics are slowly added. Agitation is maintained for 15 minutes after which, using a peristaltic pump, the mixed product is withdrawn and made to flow onto a doctor blade assembly heated to 30° C., through which there passes a siliconized polyester support web on which the product is deposited as a film to a thickness of 70 microns. The product deposited as a film on the polyester web is passed through a forced-air oven heated to 35° C. On leaving the oven the film is detached from the polyester support, it is die-cut with a roller die into 4.6×6.6 cm rectangles. The rectangles obtained in this manner from the film are packaged in a sealed container.

Each rectangle obtained has a thickness of 45 microns, the time for its dissolving in water being 7 seconds. The quantities of the microorganisms present were measured by a microscope, the result being the following:

| | |
|---|---|
| weight of rectangle (4.6 × 6.6 cm) | 136 mg |
| quantity of lactobacillus paracasei | 1.5 × 10³ u |

The invention claimed is:

1. A soluble solid film for treating milk to produce dairy products, comprising:
    at least one oxidized starch,
    at least one cellulose, and
    at least one milk treatment bacterium,
    wherein the cellulose is selected from the group consisting of hydroxypropylmethylcellulose, hydroxyethylcellulose, hydroxypropylcellulose and carboxymethylcellulose,
    wherein the milk treatment bacterium is incorporated into a solid mass of the cellulose and the oxidized starch, and
    wherein the cellulose and the oxidized starch are chemically bonded to one another.

2. The soluble solid film according to claim 1, wherein the milk treatment bacteria are lactic acid cultures selected from the group consisting of probiotic, prebiotic, symbiotic cultures and mixtures thereof.

3. The soluble solid film of claim 1, wherein the milk treatment bacterium is at least one lactic acid culture selected from the group consisting of a probiotic culture, a prebiotic culture, and a symbiotic culture.

4. The soluble solid film according to claim 1, wherein the cellulose and the oxidized starch are chemically bonded by an ester bond.

5. The soluble solid film according to claim 4, wherein the cellulose is hydroxypropylmethylcellulose.

6. A soluble solid film for treating milk to produce dairy products, comprising:
- at least one oxidized starch,
- at least one cellulose, and
- at least one milk treatment bacterium dispersed in the solid film,
- wherein the cellulose is at least one selected from the group consisting of hydroxypropylmethylcellulose, hydroxyethylcellulose, hydroxypropylcellulose and carboxymethylcellulose,
- wherein the solid film is a homogeneous mixture of the oxidized starch, the cellulose and the milk treatment bacterium, and wherein the oxidized starch and the cellulose are chemically bonded together.

7. The soluble solid film of claim 6, wherein the milk treatment bacterium is at least one selected from the group consisting of a lactic acid bacteria, bifido bacteria, non-elactic acid bacteria and non-bifido bacteria.

8. The soluble solid film of claim 6, wherein the milk treatment bacterium includes lactic acid bacteria.

9. The soluble film of claim 6, wherein the cellulose is at least one selected from the group consisting of hydroxypropylmethylcellulose and hydroxyethylcellulose.

10. The soluble solid film of claim 6, wherein the cellulose is present in an amount of from 27 to 70% by weight based on the total weight of the solid soluble film.

11. The solid soluble film of claim 6, wherein the cellulose is present in an amount of from 32 to 70% by weight based on the total weight of the soluble solid film.

12. The soluble solid film of claim 6, wherein the cellulose is present in an amount of from 41 to 70% by weight based upon the total weight of the soluble solid film.

13. The solid soluble film of claim 6, having a thickness of between 10 and 70 microns.

14. The soluble solid film of claim 6, wherein the milk treatment bacterium is at least one selected from the group consisting of lyophilized *streptococcus thermophilus,* lyophilized *lactobacillus rhamnosus,* lyophilized bifido bacterium breve, lyophilized *lactobacillus casei,* and lyophilized *lactobacillus paracasel.*

15. A process, comprising:
- mixing the soluble solid film of claim 6 with milk to form a culture mixture, and
- forming a dairy product from the culture mixture.

16. The soluble solid film according to claim 6, wherein the cellulose and the oxidized starch are chemically bonded by an ester bond.

17. The soluble solid film according to claim 16, wherein the cellulose is hydroxypropylmethylcellulose.

* * * * *